(12) United States Patent
DeHaan

(10) Patent No.: US 11,314,384 B2
(45) Date of Patent: *Apr. 26, 2022

(54) SYSTEM AND USER INTERFACE FOR CLINICAL REPORTING AND ORDERING PROVISION OF AN ITEM

(71) Applicant: CERNER INNOVATION, INC., Kansas City, KS (US)

(72) Inventor: Jan DeHaan, Downington, PA (US)

(73) Assignee: CERNER INNOVATION, INC., North Kansas City, MO (US)

( * ) Notice: Subject to any disclaimer, the term of this patent is extended or adjusted under 35 U.S.C. 154(b) by 206 days.

This patent is subject to a terminal disclaimer.

(21) Appl. No.: 16/828,158

(22) Filed: Mar. 24, 2020

(65) Prior Publication Data

US 2020/0225816 A1 Jul. 16, 2020

Related U.S. Application Data

(63) Continuation of application No. 12/016,278, filed on Jan. 18, 2008, now Pat. No. 10,635,260.

(60) Provisional application No. 60/885,927, filed on Jan. 22, 2007.

(51) Int. Cl.
  *G16H 20/00* (2018.01)
  *G06F 3/0482* (2013.01)
  (Continued)

(52) U.S. Cl.
  CPC ........... *G06F 3/0482* (2013.01); *G16H 10/20* (2018.01); *G16H 10/60* (2018.01); *G16H 20/10* (2018.01); *G16H 40/20* (2018.01)

(58) Field of Classification Search
  None
  See application file for complete search history.

(56) References Cited

U.S. PATENT DOCUMENTS 4,847,764 A  7/1989  Halvorson et al.
5,077,666 A  12/1991  Brimm et al.
(Continued)

FOREIGN PATENT DOCUMENTS

EP  0090971 A1  10/1983
EP  0950971 A2  10/1999
(Continued)

OTHER PUBLICATIONS

Bertino et al., "A Flexible Model Supporting the Specification and Enforcement of Role-Based Authorization in Workflow Management Systems", Proceedings of the second ACM workshop on Role-based access, 1997, 12 pages.
(Continued)

*Primary Examiner* — John A Pauls
(74) *Attorney, Agent, or Firm* — Shook, Hardy & Bacon L.L.P.

(57) ABSTRACT

A user interface system enables user selection of related parameters identifying an order for providing an item or service. The system employs a repository including information identifying candidate items or services for order and associated corresponding related order parameters in which an individual item or service for order is associated with multiple related order parameters. A user interface processor for, in response to user entry of order associated data, uses the repository in providing data representing a display image. The display image includes, an initial single candidate order including multiple order related parameters, order related parameter identifiers, multiple concurrently displayed columnar image areas correspondingly associated with the multiple order related parameters and individually incorporating multiple user selectable values for a respective individual order related parameter. In response to the user selection of a first value for a first order related parameter in a first columnar image area for incorporation in the candidate order, corresponding compatible sets of order related (Continued)

parameter values are presented in remaining columnar image areas of the multiple concurrently displayed columnar image areas. The display image enables, in response to user command, user selection of a complete candidate order derived by selection of displayed order related parameter values in the concurrently displayed columnar image areas.

18 Claims, 8 Drawing Sheets

(51) Int. Cl.
*G16H 10/20* (2018.01)
*G16H 10/60* (2018.01)
*G16H 20/10* (2018.01)
*G16H 40/20* (2018.01)

(56) References Cited

U.S. PATENT DOCUMENTS

| | | |
|---|---|---|
| 5,305,205 A | 4/1994 | Weber et al. |
| 5,319,543 A | 6/1994 | Wilhelm |
| 5,530,861 A | 6/1996 | Diamant et al. |
| 5,692,125 A | 11/1997 | Schloss et al. |
| 5,721,913 A | 2/1998 | Ackroff et al. |
| 5,745,901 A | 4/1998 | Entner et al. |
| 5,758,095 A | 5/1998 | Albaum et al. |
| 5,790,119 A | 8/1998 | Sklut et al. |
| 5,799,297 A | 8/1998 | Goodridge et al. |
| 5,826,239 A | 10/1998 | Du et al. |
| 5,832,455 A | 11/1998 | Hayashi et al. |
| 5,842,173 A | 11/1998 | Strum et al. |
| 5,842,976 A | 12/1998 | Williamson |
| 5,845,300 A | 12/1998 | Comer et al. |
| 5,850,221 A | 12/1998 | Macrae et al. |
| 5,918,226 A | 6/1999 | Tarumi et al. |
| 5,923,018 A | 7/1999 | Kameda et al. |
| 5,937,388 A | 8/1999 | Davis et al. |
| 5,987,422 A | 11/1999 | Buzsaki |
| 6,024,699 A | 2/2000 | Surwit et al. |
| 6,037,940 A | 3/2000 | Schroeder et al. |
| 6,052,669 A | 4/2000 | Smith et al. |
| 6,052,684 A | 4/2000 | Du |
| 6,061,506 A | 5/2000 | Wollaston et al. |
| 6,064,984 A | 5/2000 | Ferguson et al. |
| 6,067,548 A | 5/2000 | Cheng |
| 6,073,109 A | 6/2000 | Flores et al. |
| 6,078,982 A | 6/2000 | Du et al. |
| 6,085,184 A | 7/2000 | Bertrand et al. |
| 6,088,679 A | 7/2000 | Barkley |
| 6,115,646 A | 9/2000 | Fiszman et al. |
| 6,151,583 A | 11/2000 | Ohmura et al. |
| 6,208,345 B1 | 3/2001 | Sheard et al. |
| 6,208,974 B1 | 3/2001 | Campbell et al. |
| 6,225,998 B1 | 5/2001 | Okita et al. |
| 6,278,901 B1 | 8/2001 | Winner et al. |
| 6,278,977 B1 | 8/2001 | Agrawal et al. |
| 6,279,009 B1 | 8/2001 | Smirnov et al. |
| 6,279,042 B1 | 8/2001 | Ouchi |
| 6,282,531 B1 | 8/2001 | Haughton et al. |
| 6,304,886 B1 | 10/2001 | Bernardo et al. |
| 6,308,163 B1 | 10/2001 | Du et al. |
| 6,308,188 B1 | 10/2001 | Bernardo et al. |
| 6,347,329 B1 | 2/2002 | Evans |
| 6,458,080 B1 | 10/2002 | Brown et al. |
| 6,714,913 B2 | 3/2004 | Brandt et al. |
| 6,839,678 B1 | 1/2005 | Schmidt et al. |
| 7,027,997 B1 | 4/2006 | Robinson et al. |
| 7,047,535 B2 | 5/2006 | Lee et al. |
| 7,051,071 B2 | 5/2006 | Stewart et al. |
| 7,240,324 B2 | 7/2007 | Casati et al. |
| 7,356,538 B2 | 4/2008 | Bangel et al. |
| 7,366,579 B2 | 4/2008 | Ara et al. |
| 7,386,797 B1 | 6/2008 | Chatterjee et al. |
| 7,447,644 B2 | 11/2008 | Brandt et al. |
| 7,487,435 B2 | 2/2009 | Aviv |
| 7,562,026 B2 | 7/2009 | DelMonego et al. |
| 7,590,971 B2 | 9/2009 | Ferguson et al. |
| 7,664,657 B1 | 2/2010 | Letzt et al. |
| 7,706,906 B2 | 4/2010 | Ara et al. |
| 7,778,844 B2 | 8/2010 | Ammer et al. |
| 7,809,761 B2 | 10/2010 | Ferguson |
| 8,094,521 B2 | 1/2012 | Levy |
| 8,255,225 B2 | 8/2012 | Byford et al. |
| 8,321,241 B1 | 11/2012 | Mansour et al. |
| 8,355,928 B2 | 1/2013 | Spahn |
| 8,451,101 B2 | 5/2013 | Somasundaram et al. |
| 8,457,980 B1 | 6/2013 | DeTore |
| 8,509,936 B2 | 8/2013 | Ara et al. |
| 8,521,538 B2 | 8/2013 | Laughery et al. |
| 8,566,123 B2 | 10/2013 | Mansour et al. |
| 8,621,418 B2 | 12/2013 | Cass et al. |
| 8,655,832 B2 | 2/2014 | Muller et al. |
| 8,677,319 B2 | 3/2014 | Clemm et al. |
| 8,924,224 B2 | 12/2014 | Hoffman et al. |
| 2002/0062230 A1 | 5/2002 | Morag et al. |
| 2002/0065701 A1 | 5/2002 | Kim et al. |
| 2002/0170035 A1 | 11/2002 | Casati et al. |
| 2003/0050821 A1 | 3/2003 | Brandt et al. |
| 2003/0149714 A1 | 8/2003 | Casati et al. |
| 2004/0078231 A1 | 4/2004 | Wilkes et al. |
| 2004/0122701 A1 | 6/2004 | Dahlin et al. |
| 2004/0172301 A1 | 9/2004 | Mihai et al. |
| 2004/0199405 A1 | 10/2004 | Harper et al. |
| 2005/0015279 A1 | 1/2005 | Rucker |
| 2005/0027563 A1 | 2/2005 | Fackler et al. |
| 2005/0055242 A1 | 3/2005 | Bello et al. |
| 2005/0138031 A1 | 6/2005 | Wefers |
| 2006/0122865 A1 | 6/2006 | Preiss et al. |
| 2006/0149416 A1 | 7/2006 | Mohapatra et al. |
| 2006/0173713 A1 | 8/2006 | Petro et al. |
| 2006/0195484 A1 | 8/2006 | Mahesh et al. |
| 2006/0259195 A1 | 11/2006 | Eliuk et al. |
| 2007/0143142 A1 | 6/2007 | Villasenor et al. |
| 2007/0156569 A1* | 7/2007 | Vignet .................. G06Q 40/04 705/37 |
| 2007/0233521 A1 | 10/2007 | Wehba et al. |
| 2007/0294322 A1 | 12/2007 | Besch et al. |
| 2008/0028005 A1 | 1/2008 | Cass et al. |
| 2008/0177579 A1 | 7/2008 | DeHaan |
| 2008/0244610 A1 | 10/2008 | Zhang et al. |
| 2008/0270212 A1 | 10/2008 | Blight et al. |
| 2010/0036667 A1 | 2/2010 | Byford et al. |
| 2011/0040564 A1 | 2/2011 | Laughery et al. |
| 2011/0210853 A1 | 9/2011 | Lord et al. |
| 2012/0136667 A1 | 5/2012 | Emerick et al. |
| 2013/0080190 A1 | 3/2013 | Mansour et al. |
| 2014/0324555 A1 | 10/2014 | Wu et al. |

FOREIGN PATENT DOCUMENTS

| | | |
|---|---|---|
| EP | 1065618 A2 | 1/2001 |
| WO | 1999/024927 A1 | 5/1999 |
| WO | 2000/003344 A1 | 1/2000 |
| WO | 2000/014618 A2 | 3/2000 |
| WO | 2004/034179 A2 | 4/2004 |

OTHER PUBLICATIONS

Chun et al., "Dynamic Composition of Workflows for Customized eGovernment Service Delivery", Proceedings of the 2002 Annual National Conference on Digital Government Research, May 2002, pp. 1-7.

Cugola et al., "Exploiting an Event Based Infrastructure to Develop Complex Distributed Systems", Proceedings of the 20th International Conference on Software Engineering, IEEE, 1998, pp. 261-270.

Dewan et al., "Workflow Optimization Through Task Redesign in Business Information Processes", Proceedings of the Thirty-First Hawaii International Conference on System Sciences, vol. 1, Jan. 1998, 13 pages.

(56) References Cited

OTHER PUBLICATIONS

Georgakopoulos et al., "An Overview of Workflow Management: From Process Modeling to Workflow Automation Infrastructure". Distributed and Parallel Databases, vol. 3, No. 2, Apr. 1995, pp. 119-153.
Lovis et al., "Evaluation of a Command-line Parser-based Order Entry Pathway for the Department of Veterans Affairs Electronic Patient Record", Journal of the American Medical Informatics Association,vol. 8, No. 5, Sep.-Oct. 2001, pp. 486-498.
Marazakis et al., "Management of Work Sessions in Dynamic Open Environments", Proceedings Ninth International Workshop on Database and Expert Systems Applications, IEEE, Aug. 26-28, 1998, 6 pages.
Nielsen et al., "Using Domino Workflow", Lotus, International Technical Support Organization, Available online at: <www.redbooks.ibm.com>, May 2000, 31 pages.
Payne et al., "Preparation and Use of Preconstructed Orders, Order Sets, and Order Menus in a Computerized Provider Order Entry System", Journal of the American Medical Informatics Association, vol. 10, No. 4, Jul.-Aug. 2003, pp. 322-329.
Zhao et al., "Temporal Workflow Management in a Claim Handling System", ACM SIGSOFT Software Engineering Notes, vol. 24, No. 2, 1999, pp. 187-195.

\* cited by examiner

CT ABDOMEN WITH IV CONTRAST TODAY ROUTINE. REASON: ABDOMINAL DISTENTION — 305

| MODALITY | BODY SITE | PROCEDURE | CONTRAST | TIMING | URGENCY REASON |
|---|---|---|---|---|---|
| | ABDOMEN | | WITH IV CONTRAST | TODAY | |
| | ABSCESS | ... | WITH AND WITHOUT CONTR | ... | |
| | ABDOMEN | ANGIOGRAPHY | WITH CONTRAST | AT 3 AM | |
| | ABDOMEN/RETROPERITONE | GUIDED ASPIRATION | WITH ORAL CONTRAST | AT 4 AM | |
| | ANKLE | | WITH IV CONTRAST | AT 5 AM | |
| | BONE | | WITH RECTAL GASTROGRAF | AT 6 AM | |
| | CERVICAL SPINE | | WITH IV CONTRAST | AT 7 AM | |
| | CHEST (THORAX) | | WITHOUT CONTRAST | AT NOON | |
| | ELBOW | | | AT MIDNIGHT | |
| | FACIAL BONE/SINUS | | | IN THE MORNING | |
| | FEMUR | | | IN THE EVENING | |
| | FOOT | | | TODAY | |
| | HAND | | | ON CALL TO OR | |
| | HEAD | | | IN THE OR | |
| | HIP | | | PRE-OP | |
| | MORE... | | | MORE... | |

FIG. 3

CT ABDOMEN WITH IV CONTRAST / REASON: ABDOMINAL DISTENTION — 305

| BODY SITE | | PROCEDURE | CONTRAST | TIMING URGENCY REASON |
|---|---|---|---|---|
| ABDOMEN | MODALITY | ... | WITH IV CONTRAST | |
| ABSCESS | CT | ANGIOGRAPHY | WITH AND WITHOUT CONTR | |
| ABDOMEN | CT | GUIDED ASPIRATION | WITH CONTRAST | |
| ABDOMEN/RETROPERITO | MRA | | WITH ORAL CONTRAST | |
| ANKLE | MRI | | WITH IV CONTRAST | |
| BONE | ULTRASOUND | | WITH RECTAL GASTROGRAF | |
| CERVICAL SPINE | XRAY | | WITH IV CONTRAST | |
| CHEST (THORAX) | | | WITHOUT CONTRAST | |
| ELBOW | | | | |
| FACIAL BONE/SINUS | | | | |
| FEMUR | | | | |
| FOOT | | | | |
| HAND | | | | |
| HEAD | | | | |
| HIP | | | | |
| INTERM JOINT | | | | |
| KIDNEY | | | | |
| KNEE | | | | |
| LIVER | | | | |
| LOWER EXTREMITY | | | | |
| LUNG | | | | |
| MASTOIDS | | | | |
| NECK | | | | |
| ORBIT | | | | |
| PANCREAS | | | | |
| PELVIC | | | | |
| PELVIS | | | | |
| PELVIS AND ABDOMEN | | | | |

CT ABDOMEN WITH IV CONTRAST TODAY ROUTINE. REASON: ABDOMINAL DISTENTION — 305

510

505

| MODALITY | BODY SITE | PROCEDURE | CONTRAST | TIMING URGENCY REASON |
|---|---|---|---|---|
| CT<br>CT<br>MRA<br>MRI<br>ULTRASOUND<br>XRAY | ABDOMEN<br>ABSCESS — 509<br>ABDOMEN<br>ABDOMEN/RETROPERITONE<br>ANKLE<br>BONE<br>CERVICAL SPINE<br>CHEST (THORAX)<br>ELBOW<br>FACIAL BONE/SINUS<br>FEMUR<br>FOOT<br>HAND<br>HEAD<br>HIP<br>MORE... | ....<br>ANGIOGRAPHY<br>GUIDED ASPIRATION | WITH IV CONTRAST<br>WITH AND WITHOUT CONTR<br>WITH CONTRAST<br>WITH ORAL CONTRAST<br>WITH IV CONTRAST<br>WITH RECTAL GASTROGRAF<br>WITH IV CONTRAST<br>WITHOUT CONTRAST | |

CT ABDOMEN WITH IV CONTRAST TODAY ROUTINE. REASON: ABDOMINAL DISTENTION

| PROCEDURE BODYSITE MODALITY | CONTRAST | TIMING | URGENCY | REASON |
|---|---|---|---|---|
| | WITH IV CONTRAST | TODAY | ROUTINE | ABDOMINAL DISTENTION |
| | WITH AND WITHOUT CONTR | ... | NOW | ABD PAIN |
| | WITH CONTRAST | AT 3 AM | ROUTINE | ABD PAIN - LLQ,LUQ,RLQ,RUQ |
| | WITH ORAL CONTRAST | AT 4 AM | STAT | ABD WALL ABSCESS/CELLULITIS |
| | WITH IV CONTRAST | AT 5 AM | | ABD WOUND DRAINING |
| | WITH RECTAL GASTROGRAF | AT 6 AM | | ABD PAIN, DEHYDRATION |
| | WITH IV CONTRAST | AT 7 AM | | ABD/PELV SWELLING |
| | WITHOUT CONTRAST | AT NOON | | ABDOMINAL DISTENTION |
| | | AT MIDNIGHT | | ABDOMINAL PAIN |
| | | IN THE MORNING | | ADRENAL MASS |
| | | IN THE EVENING | | ADRENAL NEOPLASM |
| | | TODAY | | APPENDECTOMY 7-9, FEVER, HIGH |
| | | ON CALL TO OR | | BILAT ADRENAL HYPERPLASIA |
| | | IN THE OR | | CHOLECYSTITIS |
| | | PRE-OP | | |
| | | MORE... | | MORE... |

FIG. 6

CT ABDOMEN WITH IV CONTRAST TODAY ROUTINE. REASON: ABDOMINAL DISTENTION — 710

| | BODY SITE | PROCEDURE | CONTRAST | TIMING |
|---|---|---|---|---|
| | ABDOMEN | ... | WITH IV CONTRAST | TODAY |
| | ABSCESS | ANGIOGRAPHY | WITH AND WITHOUT CONTR | AT 3 AM |
| | ABDOMEN | GUIDED ASPIRATION | WITH CONTRAST | AT 4 AM |
| | ABDOMEN/RETROPERITONE | | WITH ORAL CONTRAST | AT 5 AM |
| | ANKLE | | WITH IV CONTRAST | AT 6 AM |
| | BONE | | WITH RECTAL GASTROGRAF | AT 7 AM |
| | CERVICAL SPINE | | WITH IV CONTRAST | AT NOON |
| | CHEST (THORAX) | | WITHOUT CONTRAST | AT MIDNIGHT |
| | ELBOW | | | IN THE MORNING |
| | FACIAL BONE/SINUS | | | IN THE EVENING |
| | FEMUR | | | TODAY |
| | FOOT | | | ON CALL TO OR |
| | HAND | | | IN THE OR |
| | HEAD | | | PRE-OP |
| | HIP | | | |
| | MORE... | | | MORE... |

MODALITY
BODY SITE
PROCEDURE
CONTRAST
TIMING
URGENCY
REASON
— 730

FIG. 7

SYSTEM AND USER INTERFACE FOR CLINICAL REPORTING AND ORDERING PROVISION OF AN ITEM

CROSS-REFERENCE TO RELATED APPLICATIONS

This application is a continuation of copending U.S. application Ser. No. 12/016,278, titled "A System and User Interface for Clinical Reporting and Ordering Provision of an Item," filed Jan. 18, 2008, which claims the benefit of provisional application Ser. No. 60/885,927 filed Jan. 22, 2007, each of which is hereby expressly incorporated by reference in its entirety.

FIELD OF THE INVENTION

This invention concerns a user interface system enabling user selection of related parameters identifying an order for providing an item or service by selection of displayed order related parameter values in concurrently displayed columnar image areas.

BACKGROUND OF THE INVENTION

Known systems use a drop down list or popup lists to display allowable values of a data field in a form, sentence or text statement. Such a text sentence may comprise an order for an item or service such as a medication to be administered to a patient, for example. A user needs to open and interact with individual drop down lists or popup lists in generating a form, sentence or text statement. If the user wants to change a value in seven different data fields, for example, a user needs to open seven different allowable value selection lists and select a value from the individual lists. These lists are typically not displayed concurrently.

Other known systems show multiple allowable value selection lists concurrently, but such lists are static in nature, or cover only a limited number of data fields. Known systems require a relatively large number of interactions with an application and therefore involve burdensome data entry tasks and expenditure of time. A system according to invention principles addresses these deficiencies and associated problems.

SUMMARY OF THE INVENTION

A system uses a grid to display names of data fields to be valued by a user and as many co-dependent and dynamic value lists and values in each list as is practical depending on computer screen size in order to minimize a number of user computer interactions required to complete a data entry task as well as the length and duration of data entry tasks. A user interface system enables user selection of related parameters identifying an order for providing an item. The system employs a repository including information identifying candidate items for order and associated corresponding related order parameters in which an individual item for order is associated with multiple related order parameters. A user interface processor, in response to user entry of order associated data, uses the repository in providing data representing a display image. The display image includes, an initial single candidate order including multiple order related parameters, order related parameter identifiers, multiple concurrently displayed columnar image areas correspondingly associated with the multiple order related parameters and individually incorporating multiple user selectable values for a respective individual order related parameter. In response to user selection of a first value for a first order related parameter in a first columnar image area for incorporation in the candidate order, corresponding compatible sets of order related parameter values are presented in remaining columnar image areas of the multiple concurrently displayed columnar image areas. The display image enables, in response to user command, user selection of a complete candidate order derived by selection of displayed order related parameter values in the concurrently displayed columnar image areas.

BRIEF DESCRIPTION OF THE DRAWING

FIG. 3 shows a user interface display image illustrating a data entry selection grid, according to invention principles.

FIG. 4 shows a user interface display image illustrating an expanded data entry selection grid, according to invention principles.

FIG. 5 shows a user interface display image illustrating selected data entry values in a data entry selection grid associated with a chosen phrase, according to invention principles.

FIG. 6 shows a further user interface display image, according to invention principles.

FIG. 7 shows a further user interface display image embodiment, according to invention principles.

DETAILED DESCRIPTION OF THE INVENTION

Figure 1:
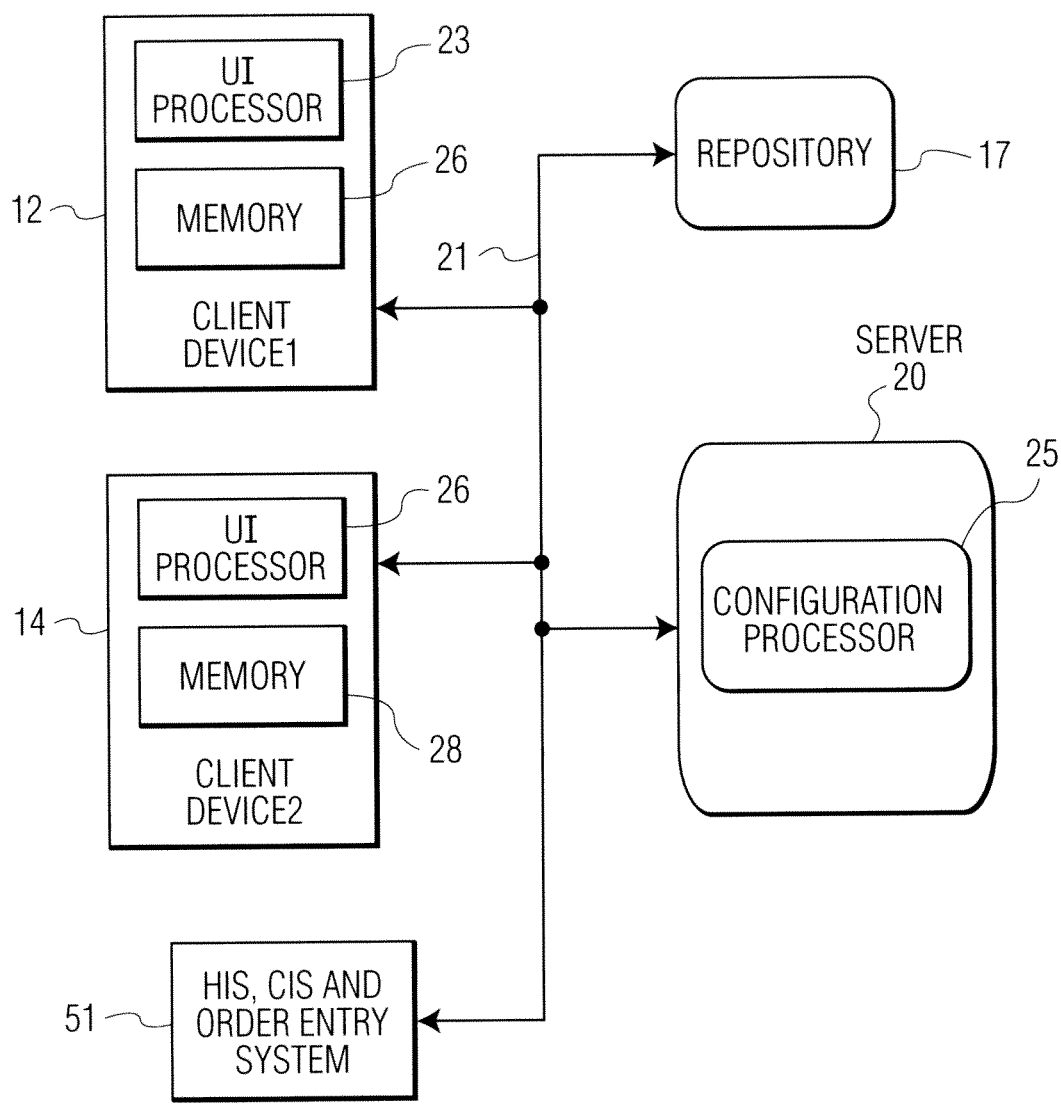
FIG. 1 shows a user interface system enabling user selection of related parameters for identifying an order for providing an item or service and for use in clinical documentation, according to invention principles.

Computerized data entry tasks often require a user to select values of multiple data fields in a form, sentence or statement, for example. A system according to invention principles uses a grid to display names of data fields to be valued by a user and as many lists of allowable values and values in each list as is practical for a selectable size of a computer screen area. Data fields are valued in response to selection of appropriate values in the lists. Multiple invisible value lists may be made visible through a single user interaction and a value list may be expanded through a single user interaction.

The system shortens time involved in performing a data entry task by concurrently displaying the most often used values in a single display image, which allows the user to select the desired values just by clicking on them or pointing to them, for example. Non-displayed lists or non-displayed values in a list can be brought into view with a single user interaction while still maintaining the advantage of being able to select values in other displayed lists. The system provides a user friendly interface for selecting values for multiple data entry fields from multiple codependent dynamic value lists with minimum user interaction.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of, hardware, firmware, and/or software.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen, microphone, or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps (e.g., of FIG. 8) herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure. Further, a document, form or record comprises a compilation of data in data fields in electronic form and is the equivalent of a paper document and may comprise a single, self-contained unit of information.

FIG. 1 shows a user interface system 10 enabling user selection of related parameters for identifying an order for providing an item or service and for use in clinical documentation. System 10 includes client devices (e.g. workstations, so called Personal Digital Assistants, cell phones) 12 and 14, repository 17, Healthcare Information System (HIS), Clinical Information System (CIS) and Order entry system 51 and server 20 inter-communicating via network 21. Server 20 includes configuration processor 25 enabling a user to determine configuration information indicating a format of an order phrase, comprising the format of a list of delimited selected values and whether a data field allows "free text" data entry or is a formula, for example. Client devices 12 and 14 individually include memory 28 and user interface processor 26. User interface processor 26 provides data representing display images for presentation on client device 12 and 14. Repository 17 includes information identifying candidate items or services for order and associated corresponding related order parameters. An individual item or service for order is associated with multiple related order parameters.

User interface processor 26, in response to user entry of order associated data, may use repository 17 and configuration processor 25 in providing data representing a display image. The display image includes, an initial single candidate order including multiple order related parameters, order related parameter identifiers and multiple concurrently displayed columnar image areas correspondingly associated with the multiple order related parameters and individually incorporating multiple user selectable values for a respective individual order related parameter. In response to user selection of a first value for a first order related parameter in a first columnar image area for incorporation in the candidate order, corresponding compatible sets of order related parameter values are presented in remaining columnar image areas of the multiple concurrently displayed columnar image areas. The display image enables, in response to user command, user selection of a complete candidate order derived by selection of displayed order related parameter values in the concurrently displayed columnar image areas.

FIG. 3 shows user interface display image 303 illustrating a data entry selection grid. Data field names and field values are displayed as a table. The sequence of table columns corresponds to a sequence in which the fields appear in the sentence, phrase, form or statement to be completed (e.g., phrase 305). The first (modality) and last (urgency, reason) visible columns 310 and 325 respectively, list data field names for which data field values cannot be displayed at this time. Other columns list body site 313, procedure 316, contrast 319 and timing 323. First column 310 displays names of any data fields in phrase 305 that precede a data field for which the values list is displayed in second column 313. Last column 325 displays the name of data fields in phrase 305 that follow the data field for which the value list is displayed in the second to last visible table column 323. Columns 313, 316, 319 and 323 display data field value lists for body site, procedure, contrast and timing data fields in phrase 305.

FIG. 4 shows user interface display image 403 illustrating an expanded data entry selection grid. If a column cannot display the possible or relevant values for a data field, the column in one embodiment is replaced by a larger column (e.g., column 413) or other display area in response to a single user interaction while other table columns remain visible. In another embodiment a column is scrolled. If phrase 305 contains words or symbols in addition to data field values, phrase 305 may be displayed in addition to the table display.

FIG. 5 shows user interface display image 503 illustrating selected data entry values in a data entry selection grid associated with a chosen phrase. Current data field values of phrase 305 are displayed in special row 505 in a table, and/or they are identified in value lists in the table columns as items 507, 509 and 513, for example. Current data field values of phrase 305 may also be individually identified in phrase 305 by field delimiters, for example (not shown to preserve drawing clarity). Similarly, original data field values (prior to the current data field values) may be indicated in a special row in the table, and/or they may be identified in value lists in the table columns or be individually identified in phrase 305 by field delimiters, for example (not shown to preserve drawing clarity). In one embodiment, the table is displayed at the bottom of a display image and occupies substantially the width of the image. The height of the table is as large as desired without obscuring relevant context information comprising information likely to be addressed by a user following selecting values of data fields in phrase 305.

In one embodiment, in response to a user selecting phrase 305, the value list table associated with phrase 305 is displayed. The lists of values of the data fields closest to a current cursor position in phrase 305 are visible. A user selects a new value for a data field just by selecting (e.g., clicking on) a desired value in a table. If a values list is not visible, the user selects a data field name in the first or last visible columns (e.g., columns 510, 525). If the user selected a data field name in first column 510 (if there are any in column 510), the data field names in visible columns 507, 509, 511 and 513 and the corresponding columns themselves shift to the right such that a selected data field and its associated column of data values is incorporated in the table. The remaining data field names in first column 510 represent data fields for which value lists are still not visible. The rightmost column 525 now lists data field names for which data field value lists in associated columns disappeared because of the right shift of the columns.

FIG. 6 shows further user interface display image 603 including a data entry and selection grid including columns of lists of data values. The values in the lists in the columns may be co-dependent. That is, selected values in one or more lists and associated columns may determine which values are included in other lists. System 10 employs different processes to indicate which values are presented in a current context indicating a previous selected data field value or values. An irrelevant value list may be hidden and replaced by a more relevant displayed value list. Irrelevant values may remain visible, but are differentiated from relevant values in a list by display attributes such as font attributes like size, color, (non-) holding, strike-through decoration, shading etc., differences in background color and texture, or through other special markings. Irrelevant values may be hidden from view as necessary to make room for values that are relevant in a current context, in response to user selection or entry of a new data value.

A data field may allow entry of free text, that is, a value that is not in the value list. In one embodiment, a cell underneath a data field name (which is displayed in the top row of a table), allows the user to enter text. Optionally the text may be constrained based on data type, e.g., the text may need to comprise a date or number, or range, a future date, or a positive integer. In addition, system 10 (FIG. 1) detects if a value entered by a user is already in a value list in a table and marks the corresponding value in the list as selected. Data fields may contain multiple values and a user may select multiple values in a list or enter multiple values as "free text" using an appropriate value delimiter such as a comma, semicolon, space character, etc. Value lists may advantageously be brought into view by clicking on a data field name in first or last visible columns 610 and 625 of display image 603. This allows a user to select a new value for that data field and if the new value requires different choices for data values in other data fields, those data fields are likely to be close to a changed data field and therefore their value lists will advantageously still be in view. Thereby, a phrase is updated by user selection of new values from lists that require no user interaction to make relevant value lists visible. Further, the number of visible value lists are maximized within the constraint of available display image space, while the content of individual visible value lists adapt to values selected by a user.

FIG. 7 shows further user interface display image 703. In this embodiment, the names of the different data fields in phrase 305 are incorporated in a single column and data fields having visible value lists in a table are identified in the single column (e.g., by different background color, different text color, check marks, etc.). A different set of data fields with associated visible value lists may be selected through scrolling data field names in the single column, selecting (e.g., by dragging) data field names (like dragging the names encompassed by white background 730 in column 710 of FIG. 7), or selection of a data field or data fields. In response to the selection of the data fields, their associated value lists are displayed. In another embodiment, data field names are placed above currently selected data field values in phrase 305. The data fields for which value lists are visible are indicated through different backgrounds, font colors, icons, or other visual attributes. The system is of particular use for clinical order entry and clinical documentation.

System 10 (FIG. 1) is applicable for creation of any order, such as, for a medication to be administered to a patient or for preparation of clinical documentation, for example, which includes documentation of patient problems, outcomes (clinical goals), assessments and findings. The system is applicable for creation of phrase 305 (FIG. 3) for a wide variety of purposes by concatenating values of one or more data fields (parameters). An individual data field has one or more allowable values and a blank value is an allowable value. A user may select more than one value for a single parameter. In that case system 10 inserts them into phrase 305 in a format in accordance with user predetermined configuration information. The format may comprise a list of (e.g., comma) delimited selected values. The last delimiter may be replaced by a word like "and" or "or", for example. A user may pre-configure delimiters to be used. The parameters that allow for multiple selections and the default delimiters for a multi-value parameter are preconfigured in system 10 (for example in a knowledge base, master file, profile, or in executable program code) using configuration processor 25.

In response to user value selection, system 10 provides data field values in different columnar sets that are compatible and are compatible with data field identifiers. The selected parameter values may be displayed in a fixed position in each column, for example, in a first row underneath a column header (data field names). That same area (cell) may be used by a user to add values not found in a data field column. Whether a parameter allows for such "free text" data entry is preconfigured in system 10 (for example in a knowledge base, master file, profile, or in the program code) using configuration processor 25. A user may select or enter a formula as a data field value. Phrase 305 displayed above a columnar display may indicate an original phrase prior to modification. System 10 updates phrase 305 in response to a user indicating that value selection/data entry is complete for the phrase. Alternatively, system 10 may update phrase 305 (e.g., an order for medication to be administered to a patient) displayed above a columnar value list by user selection or entry of new values. If some data field values are not visible, a user has the option to increase the size of the column to display more values. The column reverts to its original size in response to user selection of a table element outside of the column. In response to user input, system 10 updates a displayed data table to reflect compatible data field values and compatible data field values. System 10 may also indicate in addition to a currently selected value, the value that is most appropriate. This allows a user to more easily find the most appropriate value.

In operation of system 10, phrase 305 comprises patient care statements (stated goals (desired outcomes) of clinical care) such as "stage 4 pressure ulcer to improve to less than full thickness and length/width to _x_cm in the next 90 days" or "Will maintain SBP >100 and <170, DBP>50 and <100, Pulse>60 and <100". These examples show parts of a phrase that a user may change using the system for clinical documentation and reporting based on individual patient circumstances. For example, a user may want to change a cancer stage number, the length/width and the time period in the first example and the specific systolic and diastolic blood pressure levels to be maintained in the second example. Another example concerns clinical findings regarding pain levels, which include factors like severity, onset (sudden, constant), frequency, duration, character (dull, sharp, etc.) and anatomical body site. These factors have a list of allowable values. In a further example, phrase 305 comprises "Patient reports severe head pain. Pain occurs 3 to 4 times per day, has a sudden onset and generally subsides after about 15 minutes" and individual parts of the phrase may be varied by selecting another value of a list of allowable or suggested values.

Figure 2:
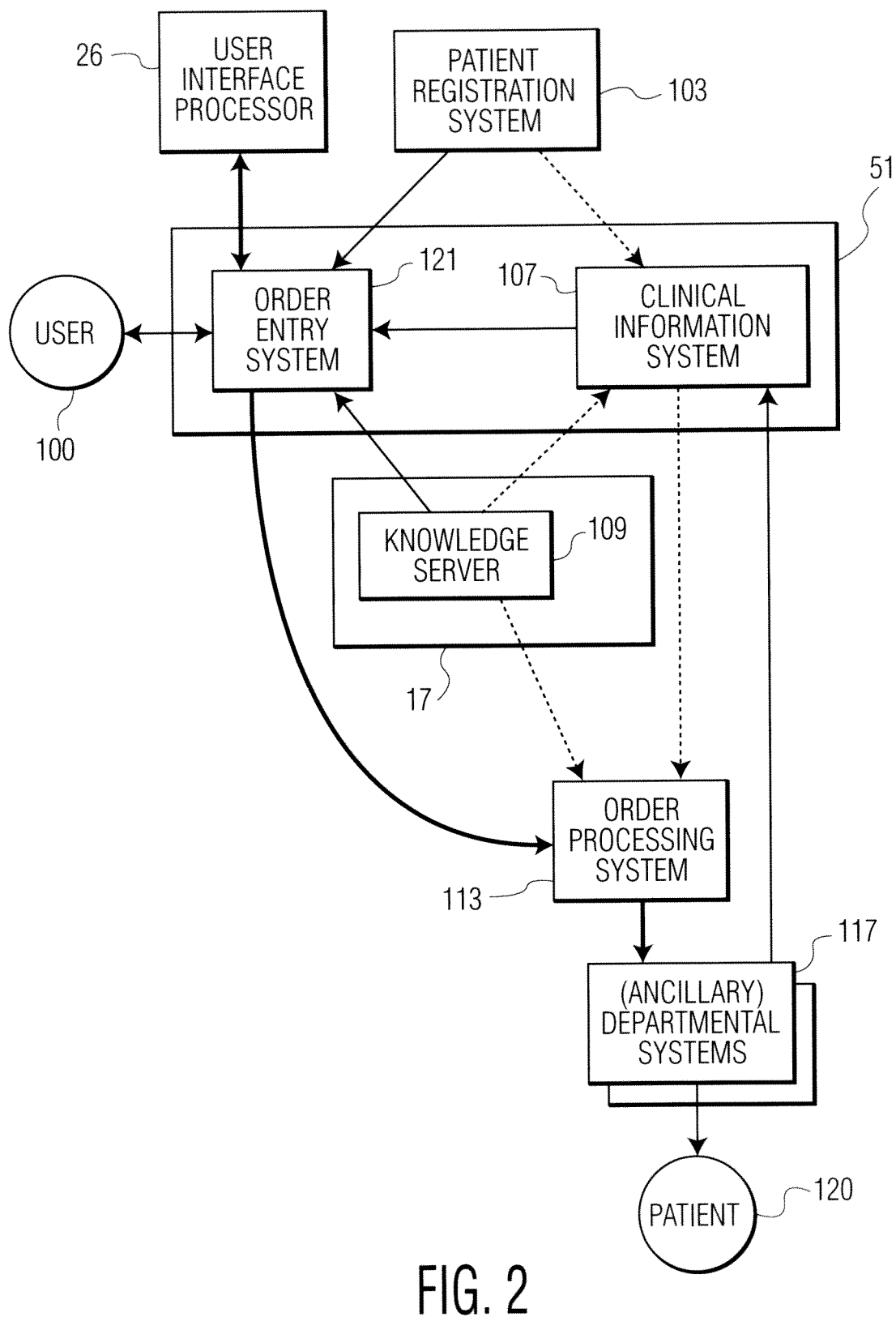
FIG. 2 shows a system overview and interaction enabling user selection of related parameters for identifying an order for providing an item or service and for use in clinical documentation, according to invention principles.

FIG. 2 shows a system overview and interaction enabling user selection of related parameters for identifying an order for providing an item and for use in clinical documentation. Specifically, FIG. 2 is described in the exemplary context of a clinical order entry (and reporting) system. User 100 such as a doctor or other clinician uses user interface processor 26 in conjunction with system 51 to enter an order for administering medication to patient 120 into order entry system 121. Order entry system 121 (in unit 51 FIG. 1) communicates data representing the entered order to order processing system 113 which validates the order and distributes it to ancillary departmental systems 117. A healthcare worker uses departmental systems 117 to view the order to determine what diagnostic or therapeutic services to render to patient 120. Order data modification data and order status information are communicated by departmental systems 117 to Clinical Information system 107 (in unit 51 FIG. 1). Order entry system 121 retrieves data from Clinical Information System 107, Knowledge Base Server 109 in repository 17 and Patient Registration System 103 and uses the retrieved data and user entered commands and data to determine a candidate order phrase to display to the user for selection. For this purpose, order entry system 121 with user interface processor 26, determines order parameters (data fields) to incorporate in the candidate order phrase as well as content of value lists for parameters. In other embodiments order processing system 113 and other units of FIG. 2 may be incorporated in unit 51, user interface processor 26, server 20 or repository 17 (FIG. 1).

Figure 8:
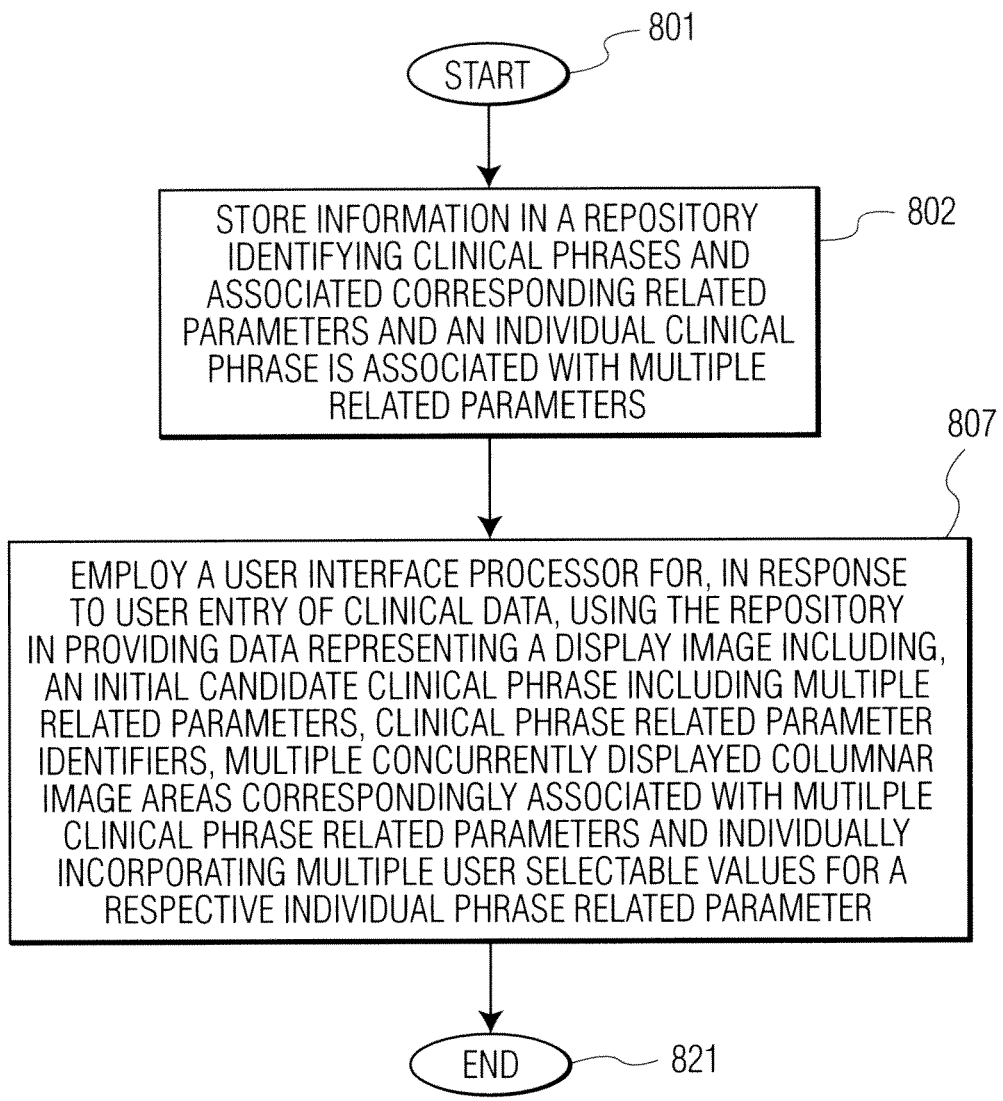
FIG. 8 shows a flowchart of a process performed by a user interface system enabling user selection of related parameters for identifying an order for providing an item and for use in clinical documentation, according to invention principles.

FIG. 8 shows a flowchart of a process performed by a user interface system 10 (FIG. 1) enabling user selection of related parameters for identifying an order for providing an item or for use in clinical documentation, for reporting and other purposes. In step 802 following the start at step 801, system 10 stores data in repository 17 including information identifying clinical phrases and associated corresponding related parameters in which an individual clinical phrase is associated with multiple related parameters. An order comprises an order for providing medical treatment for a patient and the related parameters identify at least one of, (a) quantity, (b) a route of administration of a medical treatment, (c) a frequency of administering a treatment and (d) a form of medical treatment. The form of medical treatment comprises one or more of, a package type, a strength of a medical treatment, and a concentration of a medical treatment.

In step 807, user interface processor 26, in response to user entry of clinical data, uses repository 17 and/or configuration processor 25 in providing data representing a display image. The display image includes, an initial candidate clinical phrase (order) including multiple candidate order related parameters, clinical phrase related parameter identifiers and multiple concurrently displayed columnar image areas correspondingly associated with multiple clinical phrase related parameters and individually incorporating multiple user selectable values for a respective individual phrase related parameter. The multiple values for the respective single individual order related parameter are incorporated in the candidate order in a predetermined format. Further, the initial single candidate order is a complete order or a portion of a complete order. The candidate order is updated in response to a value selection in a columnar image area or user entry of a command indicating value selection for parameters of the candidate order is complete.

A candidate item for order may compose clinical documentation including documentation of a patient problem such as, a treatment outcome, a patient assessment and clinical findings. In response to user selection of a first value for a first clinical phrase (order) related parameter in a first columnar image area for incorporation in the candidate clinical phrase, corresponding compatible sets of clinical phrase related parameter values are presented in remaining columnar image areas of the multiple concurrently displayed columnar image areas. The corresponding compatible sets of order related parameter values are compatible with the parameters identifiers. In response to user selection of a first value (which may comprise a formula, for example) for a first order related parameter, the first value is incorporated in the candidate order in predetermined position in a data field and the data field supports user entry of text.

A columnar image area comprises a vertical area vertically adjacent an associated order related parameter and having a width substantially vertically aligned and encompassing the associated order related parameter in the initial single candidate order. The display image includes as many columnar image areas correspondingly associated with the multiple order related parameters as substantially fit within an available display screen image area. In one embodiment, a columnar image area indicates a value deemed most appropriate based on other selected values for parameters of the candidate order and enables a user to select multiple values for a respective single individual order related parameter. The display image enables, in response to user command, user selection of a complete candidate clinical phrase derived by selection of displayed clinical phrase related parameter values in the concurrently displayed columnar image areas.

The display image includes a data item identifying an additional user selectable order related parameter of the initial single complete candidate order available for display together with associated selectable values in a columnar image area and not currently displayed. The data item identifies the additional user selectable order related parameters being displayed adjacent to the columnar image areas. In response to user selection of the data item identifying the additional user selectable order related parameter, the display image is updated to include the additional user selectable order related parameter and associated selectable values in a columnar image area and to exclude a previously displayed order related parameter and associated columnar image area. The display image also includes multiple data items identifying additional user selectable order related parameters of the initial single complete candidate order, available for display together with associated selectable values in columnar image areas, and not currently displayed. The data items identifying the additional user selectable order related parameter are displayed in an order corresponding to the order in which the additional user selectable order related parameters occur in the initial single candidate order. The process of FIG. 8 terminates at step 821.

The systems and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system supports user generation of a phrase from data fields using a table (or grid) to display names of data fields to be valued by a user and lists of allowable values and values in each list, selectable by a user. The processes and applications may in alternative embodiments, be located on one or more (e.g., distributed) processing devices accessing a network linking the elements of FIG. 1. Further, any of the functions and steps provided in FIGS. 1-8 may be implemented in hardware, software or a combination of both and may reside on one or more processing devices located at any location of a network linking the elements of FIG. 1 or another linked network including the Internet.

What is claimed is:

1. A clinical reporting and documentation system including at least one processing device for enabling user selection of related parameters for generating reports and clinical documentation, comprising:
   a repository including information identifying candidate items for a particular patient comprising corresponding related parameters, an individual item comprising a plurality of related parameters; and
   one or more computer storage media storing computer-usable instructions that, when used by the one or more processors, cause the one or more processors to:
   display, in response to user entry of data, an image via a user interface including at least an initial candidate item, wherein the initial candidate item includes a plurality of related parameters, and related parameter identifiers;
   generate a plurality of substantially adjacent concurrently displayed columnar image areas including a first columnar image area, the plurality of substantially adjacent concurrently displayed columnar image areas defining a column table, the column table footprint having a fixed width,
     wherein each columnar image area individually presents a corresponding different one of the plurality of related parameters and incorporating a plurality of user selectable values for a respective related parameter;
   shift, in response to user selection of an element associated with the first columnar image area, displayed columnar image areas laterally, enabling a column of data items associated with the selected element to be incorporated in the display image; and
   dynamically present, in response to user selection of a first value for a first parameter in a columnar image area for incorporation in said initial candidate item, corresponding compatible sets of related parameter values in the remaining columnar image areas of said plurality of concurrently displayed columnar image areas enabling user selection of a complete candidate item.

2. A system according to claim 1, wherein
   said columnar image areas have respective individual column names and a rightmost column lists column names for which columnar image areas disappeared because of the lateral shift of the columns, and
   said element associated with said first columnar image area is a column name.

3. A system according to claim 2, wherein said first columnar image area is a leftmost columnar image area.

4. A system according to claim 1, wherein a columnar image area comprises a vertical area vertically adjacent an associated related parameter and having a width substantially vertically aligned and encompassing said associated related parameter in said initial candidate item.

5. A system according to claim 1, wherein said display image includes as many columnar image areas correspondingly associated with said plurality of related parameters as substantially fit within an available display screen image area.

6. A system according to claim 1, wherein said initial candidate item is a portion of a complete item.

7. A system according to claim 1, wherein said initial candidate item is a complete item.

8. A system according to claim 1, wherein a candidate item comprises clinical documentation including documentation of a patient problem including at least one of, (a) a treatment outcome, (b) a patient assessment and (c) clinical findings.

9. A system according to claim 1, wherein said first columnar image area is a rightmost columnar image area.

10. A system according to claim 1, wherein
    a columnar image area enables a user to select a plurality of values for a respective single individual related parameter; and
    said plurality of values for said respective individual order related parameter are incorporated in said candidate item in a predetermined format.

11. A system according to claim 1, wherein said corresponding compatible sets of related parameter values are compatible with said parameters identifiers.

12. A system according to claim 1, wherein said first value may comprise a formula.

13. A system according to claim 1, wherein
    said candidate item is updated in response to at least one of, (a) a value selection in a columnar image area and (b) user entry of a command indicating value selection for parameters of said candidate item is complete.

14. A system according to claim 1, wherein a columnar image area indicates a value deemed most appropriate based on other selected values for parameters of said candidate item.

15. A system according to claim 14, wherein the columnar image area indicates the value deemed most appropriate based on other selected values for parameters of said candidate item by dynamically updating provided values based on one or more user selections.

16. A method for providing a clinical reporting system employing at least one processing device enabling user selection of related parameters identifying an item, comprising the activities of:

storing information identifying candidate items for a particular patient comprising corresponding related parameters, an individual item comprising a plurality of related parameters;

displaying, in response to user entry of data, an image via a user interface including at least an initial candidate item, wherein the initial candidate item includes a plurality of related parameters, and related parameter identifiers;

generating a plurality of substantially adjacent concurrently displayed columnar image areas including a first columnar image area, the plurality of substantially adjacent concurrently displayed columnar image areas defining a column table, the column table footprint having a fixed width, wherein each columnar image area individually presents a corresponding different one of the plurality of related parameters and incorporating a plurality of user selectable values for a respective related parameter;

shifting, in response to user selection of an element associated with the first columnar image area, displayed columnar image areas laterally, enabling a column of data items associated with the selected element to be incorporated in the display image; and dynamically presenting, in response to user selection of a first value for a first related parameter in a columnar image area for incorporation in said initial candidate item, corresponding compatible sets of order related parameter values in the remaining columnar image areas of said plurality of concurrently displayed columnar image areas enabling user selection of a complete candidate item.

17. A method according to claim 16, further comprising generating the complete candidate item based on at least the user selection of the first value.

18. A method according to claim 17, wherein the generation of the complete candidate item is updated based on additional user selections of additional values.

* * * * *